United States Patent
Pryor et al.

(10) Patent No.: US 9,504,847 B2
(45) Date of Patent: Nov. 29, 2016

(54) METHOD FOR PERFORMING PHOTOTHERAPY

(75) Inventors: Brian Pryor, Newark, DE (US); Sean Xiaolu Wang, Wilmington, DE (US)

(73) Assignee: BWT Property, Inc., Newark, DE (US)

( * ) Notice: Subject to any disclaimer, the term of this patent is extended or adjusted under 35 U.S.C. 154(b) by 848 days.

(21) Appl. No.: 12/964,779

(22) Filed: Dec. 10, 2010

(65) Prior Publication Data

US 2011/0144726 A1 Jun. 16, 2011

Related U.S. Application Data

(60) Provisional application No. 61/285,789, filed on Dec. 11, 2009.

(51) Int. Cl.
*A61N 5/06* (2006.01)

(52) U.S. Cl.
CPC ..... *A61N 5/0613* (2013.01); *A61N 2005/0644* (2013.01)

(58) Field of Classification Search
CPC .................... A61N 5/0613; A61N 2005/0644
USPC ....................................... 607/88–95; 128/898
See application file for complete search history.

(56) References Cited

U.S. PATENT DOCUMENTS

| 5,464,436 | A | 11/1995 | Smith |
| 6,454,791 | B1 | 9/2002 | Prescott |
| 7,527,737 | B2 | 5/2009 | Wang |
| 2009/0110712 | A1* | 4/2009 | Hyde et al. ................ 424/423 |

OTHER PUBLICATIONS

"Connection Between Oxidative Stress, Nitric Oxide and Asymmetric Dimethylarginine in Light of Clinical and Basic Science" Toth, Janos, 2007.*
"Nitric Oxide Donors and Cardiovascular Agents Modulating the Bioactivity of Nitric Oxide: An Overview", Ignarro, Louis J., Napoli, Claudio, Loscalzo, Joseph, Circulation Research 2002, 90:21-28, 2002.*

* cited by examiner

*Primary Examiner* — Aaron Roane

(57) ABSTRACT

An improved method for performing phototherapy. The method comprises a step of applying a supplement to the patient before/after light treatment, which produces nitric oxide in the subject biological tissue to be treated. The nitric oxide serves as signaling molecules to cause vasodilatation and increase blood flow and micro-circulation in the biological tissue so as to enhance the effect and reduce the required treatment time of phototherapy.

8 Claims, 1 Drawing Sheet

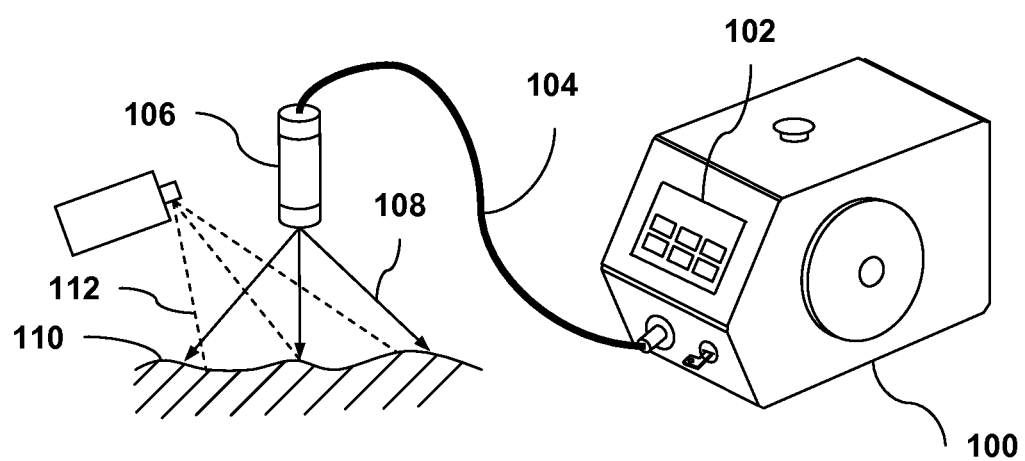

_US 9,504,847 B2_

METHOD FOR PERFORMING PHOTOTHERAPY

REFERENCE TO RELATED APPLICATION

This application claims an invention which was disclosed in Provisional Patent Application No. 61/285,789, filed Dec. 11, 2009, entitled "METHOD FOR PERFORMING PHOTOTHERAPY". The benefit under 35 USC §119(e) of the above mentioned U.S. Provisional Applications is hereby claimed, and the aforementioned application is hereby incorporated herein by reference.

FIELD OF THE INVENTION

This invention relates to a method for performing phototherapy.

BACKGROUND

Phototherapy is a medical and veterinary technique which uses lasers, LEDs (light emitting diodes), or other types of light sources to stimulate or inhibit cellular function. Recently, this technique has been widely used for treating soft tissue injury, chronic pain, and promoting wound healing for both human and animal targets.

It was shown that the effectiveness of phototherapy is affected by the micro-circulation condition of the subject biological tissue. Unfortunately, none of the current available phototherapy system possesses the capability of directly controlling the micro-circulation of the biological tissue. As a result, these systems are incapable of producing consistent therapeutic results.

SUMMARY OF THE INVENTION

It is the overall goal of the present invention to solve the above mentioned problems and provide an improved method for performing phototherapy. The method comprises a step of applying a supplement to the patient before/after light treatment, which produces nitric oxide in the subject biological tissue to be treated. The nitric oxide serves as signaling molecules to cause vasodilatation and increase blood flow and micro-circulation in the biological tissue so as to enhance the effectiveness of phototherapy.

BRIEF DESCRIPTION OF THE FIGURES

The accompanying FIGURES, where like reference numerals refer to identical or functionally similar elements throughout the separate views and which together with the detailed description below are incorporated in and form part of the specification, serve to further illustrate various embodiments and to explain various principles and advantages all in accordance with the present invention.

FIG. 1 shows an exemplary embodiment of the improved phototherapy method.

Skilled artisans will appreciate that elements in the FIGURES are illustrated for simplicity and clarity and have not necessarily been drawn to scale. For example, the dimensions of some of the elements in the FIGURES may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of method steps and apparatus components related to an improved phototherapy method. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

FIG. 1 shows an exemplary embodiment of the improved phototherapy method. In the first step of the method, a spray of _Morinda Citrifolia_ (noni) plant extract 112 is applied onto the surface of the biological tissue (e.g. skin tissue) 110. The noni extract 112 serves as a supplement to be absorbed by the tissue 110 and produce nitric oxide (NO), which acts as signaling molecules that cause smooth muscle surrounding blood vessels to relax, thus resulting in vasodilatation (widening of blood vessels) and increased blood flow and micro-circulation.

In the second step of the method, therapeutic light 108 is applied to the biological tissue 110 for performing phototherapy. The therapeutic light 108 is produced by a diode laser light source 100 and delivered through an optical fiber 104 to an output wand 106. The laser light source 100 may comprise a plurality of diode lasers with different output wavelengths. A touch-screen based user interface 102 allows the user to control the parameters (e.g. output power, wavelength, treatment time, and pulsing parameters) of the laser light source 100. The output wand 106 provides further control of the power density of the therapeutic light 108, which is applied onto the biological tissue 110. The output wavelength of the laser light source 100 preferably falls in the near infrared (NIR) region so that the laser light can penetrate deeper into the tissue. The therapeutic light 108 produces photochemical reaction in the biological tissue 110, e.g. up-regulation and down-regulation of adenosine triphosphate (ATP), reactive oxygen species, and nitric oxide. The photochemical reaction in turn produces the following therapeutic effects: (i) stimulating white blood cell activity; (ii) accelerating macrophage activity, growth factor secretion and collagen synthesis; (iii) promoting revascularization and micro-circulation; (iv) increasing fibroblast numbers and collagen production; (v) accelerating epithelial cell regeneration and speeding up wound healing; (vi) increasing growth-phase-specific DNA synthesis; (vii) stimulating higher activity in cell proliferation and differentiation; (viii) increasing the intra and inter-molecular hydrogen bonding.

The nitric oxide (NO) induced increase in blood flow and micro-circulation not only speeds up toxin removal and nutrient/oxygen transportation in the biological tissue but also facilitates the transportation of the products of the photochemical reaction. Hence both the tissue under direct laser illumination and the surrounding tissues can benefit from the above disclosed phototherapy effects. As a result, the effectiveness of the therapeutic light 108 is greatly enhanced. In the meantime, the required treatment time can be reduced.

In a slight variation of the present embodiment, a noni extract 112 is applied to the biological tissue 110 after the phototherapy procedure such that the effects of phototherapy can be maintained and prolonged before next laser treatment.

In yet another variation of the present embodiment, the noni extract can be mixed with other supplements, e.g. emu oil, to further enhance the effect of phototherapy. It is also possible to use a cooling agent together with the noni extract for cooling down the skin or dampening the fur of animals, thus resulting in a more comfortable treatment and avoiding laser induced tissue damage. In addition to the noni extract, other types of supplements (e.g. nitroglycerin, amyl nitrite) can be used as well for producing nitric oxide (NO) in the biological tissue. The supplement can be applied in other forms such as tablets, sprays, patches, and ointments. The therapeutic light can be produced by other types of light sources such as light emitting diodes (LEDs).

In the foregoing specification, specific embodiments of the present invention have been described. However, one of ordinary skill in the art appreciates that various modifications and changes can be made without departing from the scope of the present invention as set forth in the claims below. The numerical values cited in the specific embodiment are illustrative rather than limiting. Accordingly, the specification and FIGURES are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. A method for treating a biological tissue with phototherapy, the method comprising the steps of:
   producing a therapeutic light capable of being absorbed by the biological tissue to produce a photochemical reaction in the biological tissue;
   providing a supplement capable of being absorbed by the biological tissue to produce nitric oxide (NO) thereof to cause vasodilatation and increased blood flow and micro-circulation in the biological tissue;
   applying the therapeutic light to the biological tissue to produce a photochemical reaction in the biological tissue; and
   applying the supplement to the biological tissue to cause vasodilatation and increased blood flow and micro-circulation in the biological tissue, wherein said vasodilatation and increased blood flow and micro-circulation facilitates transportation of products of said photochemical reaction.

2. The method of claim 1, wherein said supplement is applied to the biological tissue before applying the therapeutic light.

3. The method of claim 1, wherein said supplement is applied to the biological tissue after applying the therapeutic light.

4. The method of claim 1, wherein said supplement comprises an extract from *Morinda Citrifolia* (noni) plant.

5. The method of claim 1, wherein said supplement comprises nitroglycerin.

6. The method of claim 1, wherein said supplement comprises amyl nitrite.

7. The method of claim 1, wherein said therapeutic light is produced by a laser light source.

8. The method of claim 1, wherein said therapeutic light is produced by a light emitting diode (LED) light source.

* * * * *